United States Patent [19]

Bergfeld et al.

[11] Patent Number: 5,459,249
[45] Date of Patent: Oct. 17, 1995

[54] PROCESS FOR CONTINUOUS MANUFACTURE OF ALKYLGLYCOSIDES

[75] Inventors: Manfred J. Bergfeld, Erlenbach; Jürgen Seifert, Grosswallstadt, both of Germany

[73] Assignee: Akzo Nobel N.V., Arnhem, Netherlands

[21] Appl. No.: 214,630

[22] Filed: Mar. 18, 1994

[30] Foreign Application Priority Data

Mar. 19, 1993 [EP] European Pat. Off. .............. 93104599

[51] Int. Cl.⁶ ..................................................... C07H 3/02
[52] U.S. Cl. ........................ 536/18.6; 536/4.1; 536/18.5; 536/124
[58] Field of Search ..................................... 536/4.1, 18.5, 536/18.6, 124

[56] References Cited

U.S. PATENT DOCUMENTS

| | | | |
|---|---|---|---|
| 4,223,129 | 9/1980 | Roth et al. | 536/18.6 |
| 4,874,852 | 10/1989 | Kinomura et al. | 536/18.6 |
| 4,939,246 | 7/1990 | Baur et al. | 536/18.6 |
| 4,950,743 | 8/1990 | McCurry, Jr. et al. | 536/18.6 |
| 5,003,057 | 3/1991 | McCurry et al. | 536/18.6 |
| 5,169,553 | 12/1992 | Durbut et al. | 252/99 |
| 5,173,207 | 12/1992 | Drapier et al. | 252/99 |
| 5,227,480 | 7/1993 | Oberholz et al. | 536/18.5 |
| 5,240,633 | 8/1993 | Ahmed et al. | 252/99 |
| 5,318,715 | 6/1994 | Krishnan | 252/99 |

FOREIGN PATENT DOCUMENTS

| | | |
|---|---|---|
| 0096917 | 12/1983 | European Pat. Off. . |
| 0132043 | 1/1985 | European Pat. Off. . |
| 0252241 | 1/1988 | European Pat. Off. . |
| 0362671 | 4/1990 | European Pat. Off. . |
| 0378710 | 7/1990 | European Pat. Off. . |
| 0415192 | 3/1991 | European Pat. Off. . |
| 0482325 | 4/1992 | European Pat. Off. . |
| 3927919 | 2/1991 | Germany . |
| 4137636 | 5/1993 | Germany . |
| 60-1196 | 1/1985 | Japan . |
| WO90/07516 | 7/1990 | WIPO . |
| 91/19722 | 12/1991 | WIPO . |
| 93/24504 | 12/1993 | WIPO . |

OTHER PUBLICATIONS

Recl. Trav. Chim. Pays–Bas 110, 023–024 (1991).
J. Carbohydrate Chemistry, 7(1), 263–269 (1988).
Wessel *J. Carb. Chem.* 1988, 7(1), 263–269.

Primary Examiner—Douglas W. Robinson
Assistant Examiner—Kathleen Kahler Fonda
Attorney, Agent, or Firm—Oliff & Berridge

[57] ABSTRACT

Alkylglycosides are manufactured by continuous reaction of monosaccharides with fatty alcohols in the presence of an acid catalyst, comprising continuously adding the monosaccharides, fatty alcohols, and catalysts to a continuous stirred-tank reactor (CSTR). The reaction takes place under steady-state conditions with a conversion of 97%±2.5% relative to the monosaccharide used. Water is removed continuously from the CSTR during the reaction, and the reaction mixture is removed from the CSTR in an amount which essentially corresponds to the amount of reactants and catalysts added.

22 Claims, No Drawings

PROCESS FOR CONTINUOUS MANUFACTURE OF ALKYLGLYCOSIDES

FIELD OF THE INVENTION

The invention relates to a continuous process for manufacturing alkylglycosides by reacting monosaccharides with fatty alcohols in the presence of an acid catalyst.

BACKGROUND

Alkylglycosides have been known for a long time and are used, among other things, as detergents because of their surfactant properties. The alkylglycosides whose alkyl residue contains a carbon number of at least 8 are especially interesting in this regard.

Since the alkylglycosides can be manufactured completely from renewable raw materials—they are obtained primarily from fatty alcohols, which can be obtained from natural fats, and saccharides—there has been no lack of effort to improve the processes used in industry. Thus, numerous catalyst systems have been developed to influence the primarily acid-catalyzed reaction advantageously. There has also been no lack of effort to develop processes that can be performed continuously.

Thus, in particular, there are many methods in which $C_1$–$C_4$ glycosides are produced continuously and then reacetalized in a second step with fatty alcohols to produce the actual washing-active product. These processes are generally referred to as two-stage processes.

U.S. Pat. No. 4,223,129 describes a continuous process in which polysaccharides and corresponding monoalcohols are reacted in a device in which the main reaction takes place mainly in a coiled tube. According to this U.S. patent, the process is also intended to be applicable to the reaction of alkyl alcohols with up to 18 carbon atoms. It has developed, however, that the reaction is difficult to control, the yields are not optimal, and moreover the water created in the reaction can only be drawn off at a later point in time, so that this cannot be termed a completely continuous process that operates satisfactorily.

European Patent Application No. 0 378 710 describes a process in which a heterogeneous acid catalyst is used. When the reaction mixture is no longer in contact with the catalyst, alkylglycoside is crystallized out and separated by adding an apolar solvent. The mother liquor is recycled back to the process after the solvent is separated out.

EP-A2-0 448 794 describes a process for manufacturing alkylglycosides in which alcohols are reacted with saccharides in a single stage. The process can also be operated continuously. It is necessary to carry out the reaction in the presence of a nonpolar solvent, an emulsifier, and relatively large quantities of an acid catalyst.

Although a number of processes for manufacturing alkylglycosides are already known, there is a great need for an improved single-stage fully continuous process, with the term "single-stage processing" meaning one in which the corresponding long-chain alkyl alcohol and saccharide are reacted directly with one another.

SUMMARY OF THE INVENTION

One goal of the invention therefore is to provide a process which is economical to perform, which permits direct reaction without recycling the reaction mixture, which requires no additional additives such as solvents, etc., one that works with high yields and produces products which are especially suitable as detergent raw materials, one that is flexible, and one with which it is possible to adjust the properties required for an individual application such as viscosity, average degree of polymerization (DP), interfacial tension, etc. in a deliberate and reproducible manner. The goal of the invention is also to provide alkylglycosides which are still pumpable at high solids concentrations such as 70 or 75% for example, as aqueous systems or solutions at room temperature.

These and other goals are achieved by a process of manufacturing alkylglycosides by continuous reaction of monosaccharides with fatty alcohols in the presence of an acid catalyst, comprising adding continuously at least one monosaccharide, at least one fatty alcohol, and at least one catalyst to a continuous stirred-tank reactor (CSTR), the reaction being performed under steady-state conditions with a conversion of 97%±2.5% relative to the monosaccharide added, drawing off water continuously from the CSTR, and removing the reaction mixture from the CSTR in an amount which essentially corresponds to the amount of reactants and catalyst added.

DETAILED DESCRIPTION OF PREFERRED EMBODIMENTS

It is preferable to mix the reactants and the catalyst intimately in advance and to add them continuously to the CSTR as a mixture.

Preferably the reaction is performed with a conversion of 98±1.5%. It is advantageous to perform the reaction at a temperature of approximately 80° to 160° C. The water is preferably drawn off in the form of water vapor at a pressure of 1 bar maximum. The molecular ratio of monosaccharide to fatty alcohol is preferably 1:1 to 1:20, especially 1:2 to 1:6.

Glucose is especially suitable as the monosaccharide. In a preferred embodiment of the process according to the invention, syrupy glucose is used. Finely ground glucose is also highly suitable, especially glucose with a particle size ≦30 µm; preferably finely ground glucose with an average particle diameter of 3 to 4 µm is used.

The process is advantageously homogeneously catalyzed, i.e. the catalyst is distributed homogeneously in the reaction mixture.

It is preferable to keep the water concentration in the CSTR under 1 wt. % by drawing off the water vapor. Especially suitable catalysts are those which allow homogeneous catalysis, i.e. the catalyst is distributed or dissolved homogeneously. Heterogeneous catalysis is for example when ion exchangers are used as the catalyst.

According to the invention, preferred catalysts include but are not limited to: fluorinated sulfonic acids, fluorinated sulfocarbonic acids and their esters, and sulfocarbonic acid esters, such as sulfocarbonic acid mono-, di-, tri-, and higher esters. Sulfocarbonic acids are also suitable, as are esters, primarily those derived from alcohols with 1 to 22 carbon atoms. Preferably the esters are derived from alcohols with at least 8 carbon atoms, especially from conventional fatty alcohols. In addition to aliphatic sulfocarbonic acids, corresponding cycloaliphatic aromatic and heterocyclic as well as unsaturated linear and cyclic compounds can be used. Instead of these acids, their partial or complete esters may be used as well.

The following acid catalysts listed as nonlimiting examples have proven advantageous according to the invention: sulfoacetic acid, sulfoacetic acid methyl ester, sulfoacetic acid dodecyl/tetradecyl ester, sulfosuccinic monododecyl ester, sulfosuccinic didodecyl ester/tetradecyl ester, sulfosuccinic dimethyl ester, sulfopropionic acid, ortho-, meta-, or para-sulfobenzoic acid, and their dodecyl esters, 5-sulfophthalic acid, 4-or 5-sulfoisophthalic acid mono- and didodecyl esters, 4-or 5-sulfotrimellithic acid and their esters, 4-sulfo-1,8-naphthalenedicarbonic acid and their esters.

In addition to the acids and their esters, the corresponding anhydrides may be used as well.

Fluorinated sulfonic acids that may be used according to the invention include in particular the perfluorinated sulfonic acids, especially those of an aliphatic and cycloaliphatic nature, as well as perfluorinated sulfocarbonic acids.

The following non-limiting examples of fluorinated sulfonic acids have proven advantageous as catalysts according to the invention: trifluoromethanesulfonic acid, perfluoroethanesulfonic acid, perfluoropropanesulfonic acid, perfluorobutanesulfonic acid, perfluorooctanesulfonic acid, perfluorosulfoacetic acid, perfluoroethylperfluorocyclohexanesulfonic acid, and mixtures thereof.

Mixtures of these catalysts with one another or with other known catalysts are also highly suitable.

In another preferred embodiment of the process according to the invention, a sulfocarbonic acid ester is used as the catalyst in which the alcohol from which the ester is formed is the same fatty alcohol used as a starting reactant in the reaction.

The quantity of catalyst used or of catalyst mixture used can be varied within relatively wide limits. Preferably the concentration is less than 40, and more preferably less than 30 mmol per mol of monosaccharide used. A preferred range is 1–10 mmol/mol saccharide.

The term "alkyl" in the sense of the invention means a residue of fatty alcohols with preferably 8 or more carbon atoms which can be linear or branched. The alkyl residue can be saturated aliphatic hydrocarbon residues, but can also be a typical residue of fatty alcohols like those obtained from natural fats, so that in addition to saturated residues, unsaturated residues and their mixtures are included. Fatty alcohols include both alcohols obtainable from natural products and alkanols produced synthetically.

The term "alkylglycosides" within the framework of the invention refers to compounds in which alkyl residues are bonded acetalically to mono- and/or oligomeric sugar residues (saccharide residues).

Steady-state conditions within the framework of the invention means that the actual continuous reaction is performed essentially under constant conditions, whereby "essentially constant" means within a certain tolerance range. Thus, the conversion, i.e. the quantity of reacted monosaccharide, is kept at 97%±2.5%. It is understood that suitable measures such as faster or slower addition of the reaction components can be used to control this value. In addition, the reaction temperature is generally kept constant at ±2° C. The same is essentially true in continuous operation for the filling level of the vessel, i.e. in general a range of fluctuation of ±2% around the specified full level is maintained.

It is understood that prior to the actual continuous reaction, the reaction must be started in the stirred-tank reactor until a state is reached which can be kept steady during the continuous reaction.

Start-up can be performed semicontinuously for example by initially adding all the alcohol and the respective amount of catalyst to the stirred-tank reactor and then adding only monosaccharide continuously.

It is also possible to add the reaction mixture in the desired volume ratios to an empty stirred-tank reactor and not to begin discharging from the reactor until a certain filling level and desired conversion have been reached. Finally, it is also possible to operate the stirred-tank reactor initially in a first reaction batchwise and, after a conversion of 97±2.5% is reached, switch the vessel to continuous operation, i.e. add the starting materials continuously and draw off a corresponding amount continuously. Of course, the vessel can also be filled with a prepared reaction mixture, which has the steady-state composition corresponding to the selected reaction conditions.

The starting substances, i.e. monosaccharide, especially glucose and fatty alcohol, in which the catalyst has preferably been dissolved beforehand, are added continuously to the vessel. Preferably however they are mixed in a mixing vessel using an intensive mixer, e.g. an intensive colloid mixer, so that a mixture that is as homogeneous as possible is obtained. This is then added continuously. The components, however, can also be mixed and metered in-line, i.e. using a suitable dispersing and homogenizing pump (for example a Supraton (™) pump made by Dorr-Oliver GmbH, Grevenbroich, Germany).

Preferably the mixture or the components are added at the top of the vessel, and the corresponding quantity of reacted product is drawn off continuously at an opposite point.

It is possible to add the glucose as anhydride, as monohydrate, or even as aqueous syrup. The reaction in the stirred vessel is measured by suitable temperature-measuring devices and kept at the appropriate temperature by heating or cooling. The stirred-tank reactor can be equipped for this purpose with corresponding double jackets and/or internal or external heat exchangers.

The removal of the water that results from the condensation reaction or which enters the system as part of a monohydrate or of the aqueous syrupy glucose is accomplished preferably by applying a suitable vacuum and applying thermal energy which corresponds to the required evaporation enthalpy of the water. Although it is possible to accomplish water removal at normal pressure or elevated pressure, preferably it is done at a pressure of less than 1 bar, preferably at pressures of 20–50 mbar.

The reaction temperature is preferably about 80° to 160° C.

It has proven advantageous to subject solid monosaccharides to fine grinding before they are used, so that the average grain size is less than 300 μm, especially less than 100 or 30 μm. In one preferred embodiment, the average grain size is 3 to 4 μm.

It was especially surprising that it is possible with the aid of the process according to the invention to accomplish a completely continuous process, i.e. direct synthesis of alkylglycosides starting with fatty alcohols and monosaccharides, especially from glucose. The resultant reaction mixture can be processed simply in a known fashion, i.e. separated into alkylglycoside and alcohol. The catalyst can be removed from the mixture and recirculated or remain as a residue following neutralization. Processing of the reaction mixture can also proceed continuously.

It was also highly surprising that the nearly complete saccharide conversion takes place during a reaction time which corresponds to that of processes that are conventionally performed batchwise. This is especially surprising when a stirred vessel is operated continuously with a conversion that is nearly 100%.

Another embodiment of the process according to the invention utilizes two or more stationary CSTRS connected in series instead of one CSTR, (i.e., CSTR cascade). The last CSTR vessel is operated on a steady-state basis with a conversion of 97±2.5%. This means that each CSTR, viewed separately, operates on a steady-state basis. In comparison to one another, however, different conditions can prevail in the individual CSTRS, for example different temperatures, catalyst concentrations, fatty alcohol/glucose ratios, pressures, etc.

It was also surprising that the process according to the invention provides alkylglycosides that differ advantageously from conventional products in terms of their viscosity.

Therefore, another embodiment of the invention is alkylglycosides obtainable by one of the methods described above with a viscosity of 50 to 400 mPa.s measured in a 10% aqueous solution. The viscosity is measured with a Brookfield viscometer at room temperature, spindles 2 and 3, rpm 30 and 60.

Products corresponding to the prior art have viscosities of 1300 to 1500 mPa.s.

The alkylglycosides according to the invention can thus be prepared in much higher concentrations and are still pumpable even at room temperature as 70 to 75% aqueous mixtures. This is extremely advantageous for the application and transport of these products. The foam values such as foam stability, foam height, etc. of the products are good. The surface tension values and the solubilization of fats and oils are outstanding.

Another advantage of the invention is that syrupy glucoses, like those obtained for example by acid or enzymatic hydrolysis of starch, can react directly with fatty alcohols. These syrupy glucoses contain, in addition to glucose and water, oligomers and, to a small extent, polysaccharides. Syrupy glucose can also be obtained from saccharose, obtained in turn from sugar beets for example.

The invention will now be described in greater detail with reference to the following examples:

Glucose (as anhydrite, monohydrate, or aqueous syrup) is added by a suitable metering unit (a screw dispenser for solids or a heatable metering pump for syrup) together with the fatty alcohol (FA) and the catalyst dissolved therein in the corresponding streams, constant over time, into a cooled 250 ml mixing vessel stirred by an intensive colloid mixer (Ultra Turrax (™)).

A stream constant over time (corresponding to the sum of the two partial streams mentioned above) is metered from this mixing vessel into the continuous-stirred tank reactor (CSTR), in this case a 1-liter Büchi stirred reactor with distillation fitting.

The reactor is equipped with an Intermig stirrer, a bottom drain, an internal temperature measurement device, a double jacket heater, and an evacuable outlet in the lid.

The reactor exhibits a residence time behavior under the stated operating conditions and with the accessories used which at no time differs by more than 1% from the theoretical curve.

The resultant water of reaction and possibly the water added with the glucose is drawn off continuously at the head of the reactor at reduced pressure and precipitated by an intensive cooler in a graduated vessel. The water production rate observed here is used as a measure of the conversion rate of the glucose (Glc) added (exactly 1 mol of water of reaction is produced per mol of anhydrous Glc added).

The product is drawn off at the bottom of the reactor with the corresponding stream, constant over time, with the aid of a gear pump, so that the level of the product in the reactor is constant in the range of ±2 mm at every point in time.

The end product is neutralized with NaOH at approximately 80° C. and then freed of surplus FA in known fashion with a thin-film evaporator.

The following experiments are performed according to the procedure described above in the 1-liter laboratory autoclave. The average hydrodynamic residence time (=volume of reaction mixture/volume flow of educts=γ) is obtained from the freely selectable (independent) variables:

Temperature

FA excess

Catalyst type and concentration

Particle size distribution of Glc together with the requirement for a certain Glc conversion, (e.g. ≧99%) as a dependent, i.e. not freely selectable, variable.

Following a start-up time of 5 γ, a CSTR contains merely approximately 1% of the content originally present. Usually a CSTR after this period of time is viewed as being in the steady state within the framework of measurement accuracy, i.e. the reactor contents no longer change measurably with time as far as concentration, density, or temperature, etc. are concerned.

Therefore, only those products that are obtained from a CSTR that is at steady state according to the above definition are used for ongoing and comparative studies.

EXAMPLE 1

The 1-liter Büchi reactor is filled with 500 ml of fatty alcohol Lorol S (Henkel) mixed with 2 mmol 4-sulfophthalic acid dilauryl ester per mol of FA. After heating the reactor contents to 110° C. and applying a vacuum of 20 mbar, in the manner described above, 80.4 g/h of anhydrous glucose (Cerestar (™)) with an average grain size of 4 μm and 349.8 g/h fatty alcohol Lorol S, corresponding to 4 mmol FA/mol glucose and 10 mmol 4-sulphophthalic acid dilauryl ester per mol of glucose, are added continuously to the reactor as the catalyst. The reactor is then operated as a CSTR with an average hydrodynamic residence time γ of 1.0 h. The reaction temperature is kept constant at 110° C.±1.0° C., and the reaction volume is always 500 ml ±10 ml, ensured by a corresponding removal of the product over time from the CSTR (which is not volume-constant during the start-up phase of about 5 h).

During the reaction, at 20 mbar, γ 7.9 g/h water is removed from the reactor, corresponding to ≧99% glucose conversion. After 6 h, the steady-state reaction product, which is clear and nearly white, is used for the subsequent analyses after neutralization of the catalyst and removal of the surplus FA to a 1.5% residual content.

The following values are obtained:

| | |
|---|---|
| Free glucose | 0.95 wt. % |
| Oligosaccharide content (DP ≧ 2) | 1.4 wt. % |
| Monoglucoside content ($C_{12} + C_{14}$) | 46.0 wt. % |
| Average DP of APG (alkylpolyglycoside) mixture | 1.20 |
| Viscosity in 10 wt. % aqueous solution | 110 mPa · s |

EXAMPLE 2

This example is conducted analogously to Example 1 with the exception that glucose monohydrate (Cerestar (™)) is added as the saccharide with a flowrate of 88.4 g/h.

Accordingly, 2 moles of water are released in this reaction per mol of reacted Glc.1H$_2$O.

In fact, $\geq$15.8 g/h water is drawn off from the reactor, corresponding to $\geq$98% glucose conversion.

After 6 h, as described in Example 1, a clear and nearly white reaction product is obtained.

Following neutralization of the catalyst and FA separation to 1.8 wt.%, the following analyses are obtained for the product:

| | |
|---|---|
| Free glucose | 1.9 wt. % |
| Oligosaccharide content (DP $\geq$ 2) | 1.8 wt. % |
| Monoglucoside content (C$_{12}$ + C$_{14}$) | 48.6% |
| Average DP of APG mixture | 1.25 |
| Viscosity in 10 wt. % aqueous solution | 275 mPa · s |

EXAMPLE 3

This example is conducted analogously to Example 1, but with the following changes:

1) An aqueous glucose syrup with 71.4 wt. % dry substance and a DE value (=dextrose equivalents) of 99 (Cerestar (™) CX 02660) is used as the saccharide.

2) Perfluorooctanesulfonic acid is used as the catalyst in the concentration of 10 mmol/mol glucose.

3) The reaction temperature is 120° C.

4) For the original reactor contents at the start of the test, an APG-FA-catalyst mixture is used which is obtained in a batch run from 80.4 g anhydrous glucose and 349.8 g FA Lorol S, with 10 mmol perfluorooctanesulfonic acid/mol glucose as the catalyst at 120° C. with 99.5% glucose conversion.

5) The average hydrodynamic residence time of the CSTR is 90 minutes.

6) The reactor is operated with contents of 400±10 ml.

The educt flows required for this are as follows:

Glucose syrup: 60.1 g/h

FA Lorol S: 186.6 g/h

From the reactor, $\geq$21.4 g/h water is removed corresponding to a glucose conversion of $\geq$98%.

The reaction mixture is single-phase at all times. The steady-state reaction product obtained after 8 h is slightly cloudy and light beige in color. Following neutralization of the catalyst and separation of the surplus FA to 1.9 wt. %, the following analytical results are obtained with the product:

| | |
|---|---|
| Free glucose | 0.4 wt. % |
| Oligosaccharide content (DP $\geq$ 2) | 2.8 wt. % |
| Monoglucoside content (C$_{12}$ + C$_{14}$) | 44.0 wt. % |
| Average DP of APG mixture | 1.25 |
| Viscosity in 10 wt. % aqueous solution | 125 mPa · s |

Examples 2 and 3 show that aqueous saccharides can be used advantageously as starting reaction products.

The use of aqueous syrups in particular is advantageously possible for direct glucosidation with FA, which was not previously possible in the prior art.

What is claimed is:

1. A process for manufacturing alkylglycosides by continuous reaction of monosaccharides with fatty alcohols in the presence of an acid catalyst, comprising continuously adding at least one monosaccharide, at least one fatty alcohol, and at least one catalyst to a continuous stirred-tank reactor, conducting the reaction under steady-state conditions with a conversion of 97%±2.5% relative to the monosaccharide used to produce a reaction mixture, drawing off water continuously from the continuous stirred-tank reactor, and removing reaction mixture continuously from the continuous stirred-tank reactor without recycling said reaction mixture into said continuous stirred-tank reactor.

2. A process according to claim 1, wherein said reaction mixture is continuously removed from the continuous stirred-tank reactor in an amount essentially corresponding to the amount of reactants and catalysts added.

3. A process according to claim 1, wherein said monosaccharide, fatty alcohol, and catalyst are mixed intimately with one another and continuously added as a mixture to the continuous stirred-tank reactor.

4. A process according to claim 1, wherein said reaction is performed with a conversion of 98%±1.5%.

5. A process according to claim 1, wherein said reaction is performed at a temperature of about 80° to 160° C.

6. A process according to claim 1, wherein said water is drawn off as water vapor at a pressure less than or equal to 1 bar.

7. A process according to claim 1, wherein water concentration in the continuous stirred-tank reactor is kept under 1 wt. % by drawing off water vapor.

8. A process according to claim 1, wherein the molar ratio of monosaccharide to fatty alcohol is 1:1 to 1:20.

9. A process according to claim 8, wherein the ratio of monosaccharide to fatty alcohol is 1:2 to 1:6.

10. A process according to claim 1, wherein said monosaccharide is glucose.

11. A process according to claim 10, wherein said glucose is syrupy glucose.

12. A process according to claim 10, wherein said glucose is finely ground glucose.

13. A process according to claim 12, wherein said finely ground glucose has a particle size less than 30 μm.

14. A process according to claim 12, wherein said finely ground glucose has an average particle diameter of 3 to 4 μm.

15. A process according to claim 1, wherein said catalyst comprises fluorinated sulfonic acid.

16. A process according to claim 15, wherein said catalyst comprises fluorinated sulfocarbonic acid or an ester thereof.

17. A process according to claim 1, wherein said catalyst comprises sulfocarbonic acid or sulfocarbonic acid ester.

18. A process according to claim 17, wherein said sulfocarbonic acid ester is made from an alcohol component that is the same as a fatty alcohol used in the reaction as a starting reactant.

19. A process according to claim 1, wherein the catalyst is used in an amount less than or equal to 40 mmol/mol saccharide.

20. A process according to claim 19, wherein the catalyst is used in an amount less than or equal to 30 mmol/mol saccharide.

21. A process according to claim 20, wherein the catalyst is used in an amount less than or equal to 10 mmol/mol saccharide.

22. A process according to claim 12, wherein said finely ground glucose has a particle size lees than 300 μm.

* * * * *

UNITED STATES PATENT AND TRADEMARK OFFICE
CERTIFICATE OF CORRECTION

PATENT NO. : 5,459,249
DATED : October 17, 1995
INVENTOR(S) : Manfred J. BERGFELD et al.

It is certified that error appears in the above-indentified patent and that said Letters Patent is hereby corrected as shown below:

Col. 2, line 34, change "I" to --1--.

Col. 4, line 31, change "anhydride" to --anhydrite--.

Col. 5, line 5, change "CSTRS" to --CSTRs--;

line 11, change "CSTRS" to --CSTRs--;

line 20, change "mPa.s" to --mPa·s--;

line 25, change "mPa.s" to --mPa·s--.

Col. 6, line 52, change "γ" to --≥--.

Col. 7, line 7, "Glc.1H$_2$O" to --Glc·1H$_2$O--.

Claim 22, col. 8, line 65, change "less" to --less--.

Signed and Sealed this

Thirtieth Day of January, 1996

Attest:

Attesting Officer

BRUCE LEHMAN

Commissioner of Patents and Trademarks